United States Patent
Schorer

(10) Patent No.: US 11,179,325 B2
(45) Date of Patent: Nov. 23, 2021

(54) THERAPEUTIC METHODS INVOLVING GASTROINTESTINAL IMPLANTS FOR ADMINISTERING METABOLIC AGENTS

(71) Applicant: GI Dynamics, Inc., Boston, MA (US)

(72) Inventor: Scott Schorer, Duxbury, MA (US)

(73) Assignee: GI Dynamics, Inc., Boston, MA (US)

(*) Notice: Subject to any disclaimer, the term of this patent is extended or adjusted under 35 U.S.C. 154(b) by 0 days.

(21) Appl. No.: 16/468,927

(22) PCT Filed: Dec. 12, 2017

(86) PCT No.: PCT/US2017/065879
§ 371 (c)(1),
(2) Date: Jun. 12, 2019

(87) PCT Pub. No.: WO2018/111916
PCT Pub. Date: Jun. 21, 2018

(65) Prior Publication Data
US 2020/0069574 A1   Mar. 5, 2020

Related U.S. Application Data

(60) Provisional application No. 62/432,835, filed on Dec. 12, 2016.

(51) Int. Cl.
| | | |
|---|---|---|
| *A61K 9/00* | (2006.01) | |
| *A61K 35/741* | (2015.01) | |
| *A61K 35/76* | (2015.01) | |
| *A61K 38/26* | (2006.01) | |
| *A61F 5/00* | (2006.01) | |

(52) U.S. Cl.
CPC .......... *A61K 9/0024* (2013.01); *A61K 35/741* (2013.01); *A61K 35/76* (2013.01); *A61K 38/26* (2013.01); *A61F 5/0076* (2013.01)

(58) Field of Classification Search
CPC .. A61K 9/0019; A61K 9/0031; A61K 9/0053; A61K 35/741; A61K 35/76; A61K 38/26; A61K 31/403; A61K 31/4985; A61K 31/522; A61K 9/0024; A61F 5/0076; A61P 3/04; A61P 3/10
See application file for complete search history.

(56) References Cited

U.S. PATENT DOCUMENTS

| | | | |
|---|---|---|---|
| 5,830,584 A | 11/1998 | Chen et al. | |
| 7,122,058 B2 | 10/2006 | Levine et al. | |
| 7,267,694 B2 | 9/2007 | Levine et al. | |
| 7,476,256 B2 | 1/2009 | Meade et al. | |
| 7,608,114 B2 | 10/2009 | Levine et al. | |
| 7,678,068 B2 | 3/2010 | Levine et al. | |
| 7,695,446 B2 | 4/2010 | Levine et al. | |
| 7,766,973 B2 | 8/2010 | Levine et al. | |
| 7,771,382 B2 | 8/2010 | Levine et al. | |
| 7,815,589 B2 | 10/2010 | Meade et al. | |
| 7,819,836 B2 | 10/2010 | Levine et al. | |
| 7,931,693 B2 | 4/2011 | Binmoeller | |
| 7,976,488 B2 | 7/2011 | Levine et al. | |
| 8,048,169 B2 | 11/2011 | Burnett et al. | |
| 8,109,895 B2 | 2/2012 | Williams et al. | |
| 8,211,186 B2 | 7/2012 | Belhe et al. | |
| 8,475,401 B2 | 7/2013 | Priplata et al. | |
| 8,486,153 B2 | 7/2013 | Levine et al. | |
| 8,568,488 B2 | 10/2013 | Stack et al. | |
| 8,636,683 B2 | 1/2014 | Chin et al. | |
| 8,821,429 B2 | 9/2014 | Vargas | |
| 8,834,553 B2 | 9/2014 | Melanson et al. | |
| 8,920,358 B2 | 12/2014 | Levine et al. | |
| 9,060,835 B2 | 6/2015 | Binmoeller et al. | |
| 9,265,596 B2 | 2/2016 | Shank et al. | |
| 9,278,019 B2 | 3/2016 | Thompson et al. | |
| 9,636,245 B2 | 5/2017 | Chamorro, III et al. | |
| 2005/0240279 A1 | 10/2005 | Kagan et al. | |
| 2011/0123501 A1 | 5/2011 | Chou et al. | |
| 2011/0190905 A1 | 8/2011 | Behan | |
| 2012/0095384 A1 | 4/2012 | Babkes et al. | |
| 2014/0200502 A1 | 7/2014 | Belhe et al. | |
| 2014/0243263 A1* | 8/2014 | Rothkopf | A61K 31/00 514/6.9 |
| 2014/0296770 A1 | 10/2014 | Holmes et al. | |
| 2016/0038500 A1 | 2/2016 | Klein et al. | |
| 2016/0058593 A1 | 3/2016 | Bangera et al. | |
| 2016/0213702 A1 | 7/2016 | von Maltzahn et al. | |

FOREIGN PATENT DOCUMENTS

WO    WO-2016/033011 A1    3/2016

OTHER PUBLICATIONS

International Search Report and Written Opinion for International Application No. PCT/US2017/065879, dated Feb. 13, 2018 (13 pages).
Extended European Search Report for European Application No. 17881262.4, dated Nov. 24, 2020 (9 pages).

* cited by examiner

*Primary Examiner* — Carlos A Azpuru
(74) *Attorney, Agent, or Firm* — Clark & Elbing LLP

(57) ABSTRACT

The present invention provides combination therapies for treating a metabolic disorder, such as type 2 diabetes, obesity, and related comorbidities (e.g., NASH or NAFLD)) in an individual undergoing treatment with a gastrointestinal implant. The combination therapies described herein include methods for treating an individual with a gastrointestinal implant with a metabolic agent, a bariatric procedure, and/or a microbiota modulator.

20 Claims, No Drawings

THERAPEUTIC METHODS INVOLVING GASTROINTESTINAL IMPLANTS FOR ADMINISTERING METABOLIC AGENTS

BACKGROUND OF THE INVENTION

According to the Center for Disease Control, over 10% of the population of the United States has been diagnosed with type 2 diabetes or is predicted to develop type 2 diabetes, over half of whom are clinically obese. Type 2 diabetes and obesity can be broadly characterized as metabolic disorders, which often lead to life-threatening co-morbidities including non-alcoholic steatohepatitis (NASH), non-alcoholic fatty liver disease (NAFLD), hypertension, coronary artery disease, hypercholesteremia, sleep apnea, and pulmonary hypertension.

Patients suffering from metabolic diseases typically have an aberrant physiological response to ingested food after a meal. In particular, inadequate secretion of insulin has been associated with development of metabolic disorders such as type 2 diabetes. This blunted insulin response is caused by a loss of the "incretin effect," the gut-dependent secretion of incretins (e.g., hormones such as glucagon-like peptide-1 (GLP-1) and glucose-dependent insulinotropic polypeptide (GIP)). Thus, the modulation of signaling pathways in the gastrointestinal tract is emerging as a promising approach for treating metabolic disorders, such as type 2 diabetes, obesity, and related comorbidities.

Many conventional treatments involve surgical modification of gastrointestinal anatomy. Such procedures include, for example, gastric remodeling and gastric bypass. Unfortunately, the morbidity rate for surgical procedures is alarmingly high, with at least 11% of cases requiring surgical intervention for correction. Early small bowel obstruction has been estimated to occur at a rate of between 2-6% in these surgeries, and mortality rates are reported to be approximately 0.5-1.5%. While invasive and irreversible surgery seems to be effective when successfully performed, the associated complication rates are unacceptably high. Laparoscopic techniques adapted to these procedures provide fewer surgical complications but continue to expose these patients to high operative risk in addition to requiring an enormous level of skill by the surgeon.

To address these risks, non-surgical methods involving the implantation of temporary gastrointestinal devices can be implemented to treat metabolic disorders (e.g., type 2 diabetes, obesity, and related comorbidities (e.g., NASH or NAFLD)). Devices such as gastrointestinal sleeves can modulate key hormones involved in insulin sensitivity, glucose metabolism, satiety, and food intake. However, metabolic disorders are complex diseases with multi-faceted etiologies, and individuals undergoing treatment with temporary gastrointestinal devices may require additional medical interventions. Additionally, patients often suffer from various metabolic disorder-related comorbidities (e.g., non-alcoholic steatohepatitis (NASH) or non-alcoholic fatty liver disease (NAFLD)). Thus, there is a need for combinatorial treatment approaches to support temporary gastrointestinal devices to provide comprehensive treatment strategies to individuals having metabolic disorders, such as type 2 diabetes, obesity, or related comorbidities thereof, such as NASH or NAFLD.

SUMMARY OF THE INVENTION

The present invention is directed to combination therapies for treating a metabolic disorder (e.g., type 2 diabetes, obesity, and related comorbidities (e.g., NASH or NAFLD)) in an individual undergoing treatment with a gastrointestinal implant.

In one aspect, the invention features a method for treating a metabolic disorder (e.g., type 2 diabetes, obesity, and related comorbidities (e.g., NASH or NAFLD)) in an individual undergoing treatment with a gastrointestinal implant, wherein the method includes administering one or more metabolic agents to the individual in an amount and for a duration to treat the metabolic disorder (e.g., type 2 diabetes, obesity, and related comorbidities (e.g., NASH or NAFLD)).

In some embodiments, the one or more metabolic agents includes an incretin modulator. In some embodiments, the incretin modulator may be a glucagon-like peptide-1 (GLP-1) receptor agonist. The GLP-1 receptor agonist may be liraglutide, exenatide, lixisenatide, dulaglutide, or albiglutide. The liraglutide can be administered at a dose from 0.006 mg to 3 mg. The exenatide can be administered at a dose from 0.05 μg to 10 μg. The lixisenatide can be administered at a dose from 0.1 μg to 20 μg. The dulaglutide can be administered at a dose from 0.0075 mg to 1.5 mg. The albiglutide can be administered at a dose from 0.3 mg to 50 mg.

In some embodiments, the incretin modulator includes a dipeptidyl peptidase-4 (DPP-4) inhibitor. The DPP-4 inhibitor may be sitagliptin, saxagliptin, alogliptin, or linagliptin. The sitagliptin can be administered at a dose from 0.25 mg to 100 mg. The saxagliptin can be administered at a dose from 0.025 mg to 5 mg. The alogliptin can be administered at a dose of 0.0625 mg to 25 mg. The linagliptin can be administered at a dose of 0.025 mg to 5 mg.

In some embodiments, the one or more metabolic agents can be administered by an enteral route. Alternatively, the one or more metabolic agents can be administered by a parenteral route.

In some embodiments, the one or more metabolic agents can be administered one or more times per month. In some embodiments, the one or more metabolic agents can be administered one or more times per week. In some embodiments, the one or more metabolic agents can be administered one or more times per day. In some embodiments, the one or more metabolic agents can be administered prior to treatment with the gastrointestinal implant. In some embodiments, the one or more metabolic agents can be administered during treatment with the gastrointestinal implant.

In a second aspect, the invention features a method for treating a metabolic disorder (e.g., type 2 diabetes, obesity, and related comorbidities (e.g., NASH or NAFLD)) in an individual undergoing treatment with a gastrointestinal implant, wherein the method includes one or more bariatric procedures to treat the metabolic disorder (e.g., type 2 diabetes, obesity, and related comorbidities (e.g., NASH or NAFLD)).

In some embodiments, the one or more bariatric procedures comprises a restrictive bariatric procedure. In some embodiments, the restrictive bariatric procedure includes providing a space-occupying device to an individual. For example, the space-occupying device can be an intragastric balloon. In some embodiments, the restrictive gastric procedure includes a gastroplasty procedure. For example, the gastroplasty procedure can include placing transmural tissue anchor plications in the gastric fundus and body.

In some embodiments, the one or more bariatric procedures can be administered prior to treatment with the gastrointestinal implant. Alternatively, the one or more bariatric procedures can be administered during treatment with the gastrointestinal implant.

In a third aspect, the invention features a method for treating a metabolic disorder (e.g., type 2 diabetes, obesity, and related comorbidities (e.g., NASH or NAFLD)) in an individual undergoing treatment with a gastrointestinal implant, wherein the method includes administering one or more microbiota modulators to an individual in an amount and for a duration to treat a metabolic disorder (e.g., type 2 diabetes, obesity, and related comorbidities (e.g., NASH or NAFLD)).

In some embodiments, the one or more gastrointestinal microbiota modulators includes one or more species of bacteria. For example, the treatment with one or more species of bacteria can be provided by a fecal microbiota transplant.

In some embodiments, the one or more gastrointestinal microbiota modulators includes a prescribed diet regimen. For example, the prescribed diet regimen can comprise a food enriched in one or more polyphenols, saccharides, polysaccharides, peptides, polypeptides, lipids, or any combination thereof. Additionally or alternatively, the prescribed diet regimen can include a food enriched in one or more species of bacteria.

In some embodiments, the one or more gastrointestinal microbiota modulators includes a dietary supplement. For example, the dietary supplement can be a prebiotic supplement. Additionally or alternatively, the dietary supplement can be a probiotic supplement. The prebiotic supplement can include a polyphenol, saccharide, polysaccharide, peptide, polypeptide, lipid, or any combination thereof.

In some embodiments, the one or more gastrointestinal microbiota modulators includes treatment with one or more bacteriophage.

In some embodiments, the one or more gastrointestinal microbiota modulators is administered prior to treatment the gastrointestinal implant. In some embodiments, the one or more gastrointestinal microbiota modulators is administered during treatment with the gastrointestinal implant.

In some embodiments, the one or more gastrointestinal microbiota modulators can be administered by an enteral route. In some embodiments, the one or more gastrointestinal microbiota modulators can be administered by a parenteral route.

In some embodiments, the one or more gastrointestinal microbiota modulators modifies the composition, growth, or activity of the gastrointestinal microbiota of the individual.

In another aspect, the method includes providing a gastrointestinal implant to the individual, wherein the implant comprises a sleeve, and recommending (i) one or more bariatric procedures to treat a metabolic disorder (e.g., type 2 diabetes, obesity, and related comorbidities (e.g., NASH or NAFLD)), (ii) administration of one or more metabolic agents in an amount and for a duration to treat the metabolic disorder (e.g., type 2 diabetes, obesity, and related comorbidities (e.g., NASH or NAFLD)), or (iii) administration of one or more microbiota modulators in an amount and for a duration to treat the metabolic disorder (e.g., type 2 diabetes, obesity, and related comorbidities (e.g., NASH or NAFLD)).

In some embodiments of any of the preceding methods, the metabolic disorder-related comorbidity may be type 2 diabetes, obesity, NASH, or NAFLD.

In some embodiments of any of the preceding methods, the gastrointestinal sleeve can be configured for implantation within a gastrointestinal tract at or distal to a pylorus of the individual. In some embodiments, the gastrointestinal sleeve comprises a wave anchor. For example, the wave anchor is a barbed wave anchor. In some embodiments, the wave anchor can be configured to reside distal to a pylorus of the individual.

DETAILED DESCRIPTION OF THE INVENTION

As described herein, the invention provides treatment methods (e.g., treatment with a metabolic agent, bariatric procedure, or microbiota modulator) that can be used in an individual undergoing treatment with a gastrointestinal implant. The methods of the invention may be used in the treatment and/or prophylaxis of a metabolic disorder (e.g., type 2 diabetes, obesity, and related comorbidities (e.g., NASH or NAFLD)).

As used herein, the term "bariatric surgery" or "bariatric procedure" refers to a procedure for weight loss involving modifications of the gastrointestinal tract and includes, but is not limited to procedures such as gastric banding, sleeve gastrectomy, GI bypass procedure (e.g., roux-en-Y, biliary duodenal bypass, loop gastric bypass), treatment with an intragastric balloon or other space-occupying devices, gastroplasties, aspiration therapy, endoscopic enteral anastomosis, and biliopancreatic diversion. "Endoscopic bariatric surgery" refers to any bariatric procedures associated with the use of an endoscope (e.g., a flexible tube that may include additional tools directly or indirectly associated with the tube) inserted through small incisions or natural body openings. As used herein, the term "gastroplasty" refers to surgical procedures that modify the stomach or other parts of the GI tract. For example, gastroplasty can be used to change the shape or size of the stomach. Subtypes of gastroplasty include bariatric gastroplasty, such as vertical banded gastroplasty, silicone ring vertical gastroplasty, horizontal banded gastroplasty, vertical banded gastroplasty, endoscopic sleeve gastroplasty with an overstitch endoscopic suturing device, and primary obesity surgery endolumenal.

As used herein, the term "comorbidity" or "related comorbidity" refers to one or more conditions, syndromes, diseases, or disorders that co-occur with metabolic disorders and can be either directly or indirectly linked to metabolic disorders. For example, metabolic disorder-related conditions may include type 2 diabetes, obesity, non-alcoholic fatty liver disease (NAFLD), non-alcoholic steatohepatitis (NASH), dyslipidemia, elevated serum/plasma LDL, elevated VLDL, elevated triglycerides, elevated cholesterol, plaque formation leading to narrowing or blockage of blood vessels, glucose intolerance, myocardial infarction, increased risk of hypertension/stroke, or coronary heart disease. As used herein, "diabetes mellitus type 2" or "type 2 diabetes" (also known as diabetes mellitus type 2, non-insulin-dependent diabetes (NIDDM), obesity-related diabetes, or adult-onset diabetes) refers to a metabolic disorder that is primarily characterized by insulin resistance, relative insulin deficiency, and hyperglycemia.

As used herein, an "effective amount" or "therapeutically effective amount" are used interchangeably to refer to an amount of an agent (e.g., metabolic agent or microbial modulating agent) that allows it to treat or prevent, partially or totally, type 2 diabetes, obesity, and related comorbidities (e.g., NASH or NAFLD)), as described herein. An effective amount of an agent may therefore induce a reduction in a blood sugar level and/or a loss of body weight. The effective amount will depend upon a number of factors, including biological activity, age, body weight, sex, general health, severity of the condition to be treated, as well as appropriate pharmacokinetic properties. A therapeutically effective amount of a composition of the present invention can be administered by an appropriate route in a single dose or multiple doses. Further, the dosages of the composition can be proportionally increased or decreased as indicated by the exigencies of the therapeutic or prophylactic situation.

As used herein, the term "gastrointestinal," "GI," "gastrointestinal tract," or "GI tract" refer to the entire alimentary canal, including from the mouth to the anus, and individual portions thereof, such as the esophagus, stomach, small intestine, large intestine, and rectum.

As used herein, the term "gastrointestinal implant" includes an anchor for securely positioning the device to the stomach and a sleeve to limit absorption of nutrients in the duodenum. A "sleeve," as used herein, refers to a hollow, cylindrical liner that is open at both ends and adapted to extend at least into the duodenum. Partially digested food, or chyme, passing through the GI tract passes through the interior of the sleeve. When implanted in an intestine, the sleeve may accomplish one or more of the following: limit the digestion or absorption of nutrients; delay the mixing of chyme with digestive enzymes; provide negative feedback; reduce hormone triggers; and treat diseases, such as metabolic disorders (e.g., type 2 diabetes, obesity, and related comorbidities (e.g., NASH or NAFLD)). A portion of the sleeve is comprised of a "flexible" material meaning that the material is conformable to collapse in the intestine to a small volume.

As used herein, the term "incretin" refers to a compound that directly or indirectly stimulates insulin release, inhibits glucagon release, and reduces gastric emptying. For example, incretins stimulate an increase in the amount of insulin released from the pancreas when plasma glucose levels are elevated relative to normal after food consumption, thereby leading to a decrease in blood glucose levels. Specific examples of incretins include gastric inhibitory peptide (i.e., glucose-dependent insulinotropic polypeptide, or GIP) and glucagon-like peptide-1 (GLP-1), along with their analogs and derivatives.

The term "metabolic agent" as used herein refers to any natural or synthetic substance that is therapeutically effective in the treatment or prevention of metabolic disorders (e.g., type 2 diabetes, obesity, and related comorbidities (e.g., NASH or NAFLD)) in an individual undergoing treatment with a gastrointestinal implant. Metabolic agents include "incretin modulators", which include i) agents that function as incretins (e.g., GLP-1 or GIP) or incretin mimetics (e.g., GLP-1 receptor agonists) and ii) agents that function as enhancers of the incretin response (e.g., dipeptidyl peptidase IV (DPP-4) inhibitors). Incretin modulators increase insulin secretion, decrease gastric emptying, and decrease blood glucose levels, and are thus useful in the treatment of disorders characterized by hyperglycemia (e.g., type 2 diabetes). The term "GLP-1 receptor agonist" or "GLP-1 agonist" as used herein refers to a substance (e.g., peptides or small molecules) that activate a GLP-1 receptor, such as the human GLP-1 receptor. For example, peptides that activate the human GLP-1 receptor (e.g., native GLP-1 peptide hormones GLP-1(7-37), GLP-1(7-36)amide, oxyntomodulin, exendin-3, exendin-4, glucagon, gastric inhibitory polypeptide (GIP), functional peptide analogues and derivatives thereof) as well as compounds that function similarly (e.g., exenatide, liraglutide, lixisenatide, albiglutide, dulaglutide, taspoglutide, and semaglutide). The term "dipeptidyl peptidase-4 inhibitor", as used herein, refers to a compound that exhibits inhibitory activity on the enzyme dipeptidyl peptidase IV (DPP-4), thus acting as an incretin enhancer, and includes compounds such as sitagliptin, vildagliptin, saxagliptin, linagliptin, gemiliptin, anagliptin, teneligliptin, alogliptin, trelagliptin, dutogliptin, omarigliptin, berberine, and lupeol. Other metabolic agents useful as part of the invention include metformin, sodium-glucose co-transporter 2 (SGLT-2) inhibitors (e.g., empagliflozi, canagliflozin, or dapagliflozin), sulfonylureas (e.g., glimepiride, glyburide, glipizide, glyburide, tolazamide, or tolbutamide), thiazolidinedione, and insulin.

As used herein, "restrictive gastric surgery" refers to a type of bariatric surgery that modifies the GI tract in a manner that limits the amount of a food that can be consumed and/or increases the likelihood of satiety by reducing the volume of free space available in the stomach or other parts of the GI tract (e.g., through use of a space-occupying device or by directly modifying the gastrointestinal tract). As used herein, a "space-occupying device" refers to a device that can be used in a restrictive gastric surgery to limit gastric capacity (e.g., reduce the volume of free space available in the stomach or other parts of the GI tract).

As used herein, the term "treatment" refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and improved prognosis. In some embodiments, the gastrointestinal implant is used to control metabolic disorders (e.g., type 2 diabetes, obesity, and related comorbidities (e.g., NASH or NAFLD)). In some embodiments, removal of gastrointestinal implant or administration of antibiotics is provided to delay development of a disease or to slow the progression of a disease.

As used herein, the term "microbiota" refers to the community of microorganisms that occur (sustainably or transiently) in and on an animal subject, typically a mammal such as a human, and includes eukaryotes, archaea, bacteria, fungi, and viruses (including bacterial viruses i.e., phage). By "gastrointestinal microbiota" or "GI microbiota" is meant any microbiota associated with (e.g., in or on) one or more portions of the GI tract, including indigenous or transient microbes. As used herein, the term "fecal microbiota" refers to microorganisms that are present in the gut, intestine, colon, and/or feces of a normal healthy adult human. By "fecal microbiota transplant" is meant the transfer of stool from a healthy donor into the gastrointestinal tract of a different individual for treatment or prophylactic purposes via any route of administration (e.g., via colonoscopy, naso-enteric tube, capsules.

As used herein, a "prebiotic" refers to a substance (e.g., a synthetic or natural substance in a food, a supplement, or a pharmaceutical composition) that selectively promotes the growth of beneficial bacteria or inhibits the growth or mucosal adhesion of pathogenic bacteria in the gastrointestinal tract. Prebiotics may be fermented or metabolized by the gastrointestinal microflora and/or by probiotics. For example, prebiotics can include mucopolysaccharides, oligosaccharides, polysaccharides, amino acids, vitamins, nutrient precursors and proteins. Additional non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, the terms "probiotic" and "probiotic micro-organisms" are used interchangeably to refer to food-grade microorganisms (e.g., alive, including semi-viable or weakened, and/or non-replicating microorganisms), microbial cell preparations, or components of microbial cells that could confer health benefits on the host when administered in adequate amounts, more specifically, that beneficially affect a host by improving its intestinal microbial balance, leading to effects on the health or well-being of the host. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

By "subject" or "patient" is meant any animal, e.g., a mammal (e.g., a human). A subject who is being treated for a metabolic disorder, e.g., high blood sugar, diabetes (e.g., type 2 diabetes), obesity, NASH, NAFLD, or a related comorbidity thereof, is one who has been diagnosed by a medical or veterinary practitioner as the case may be as having such a condition. Diagnosis may be performed by any suitable means. Subjects of the invention may have been subjected to standard tests or may have been identified, without examination, as one at high risk of having or developing a metabolic disorder, e.g., type 2 diabetes, obesity, NASH, NAFLD, or a related comorbidity due to the presence of one or more risk factors, such as age, genetics, or family history.

I. Treatment Indications

As described herein, the invention provides treatment methods (e.g., treatment with a metabolic agent, bariatric procedure, or microbiota modulator) that can be used in an individual undergoing treatment with a gastrointestinal implant. The methods of the invention may be used in the treatment and/or prophylaxis of a metabolic disorder (e.g., type 2 diabetes, obesity, and related comorbidities (e.g., NASH, NAFLD, high blood pressure, high cholesterol, and sleep apnea)). For example, related conditions may include disorders including NASH, NAFLD, high blood pressure, high cholesterol, sleep apnea, dyslipidemia, hyperglycemic conditions (e.g., prediabetes, insulin-independent type 2 diabetes) or physiological conditions or disorders associated thereof. Hyperglycemic conditions treatable by a method of the invention can also include a histopathological change associated with chronic or acute hyperglycemia (e.g., degeneration of pancreas (beta.-cell destruction), kidney tubule calcification, degeneration of liver, eye damage (diabetic retinopathy), diabetic foot, ulcerations in mucosa such as mouth and gums, excess bleeding, delayed blood coagulation, or wound healing). Disorders treatable also include, for example, abnormally elevated serum/plasma LDL, VLDL, triglycerides, cholesterol, plaque formation leading to narrowing or blockage of blood vessels, glucose intolerance, myocardial infarction, increased risk of hypertension/stroke, or coronary heart disease.

II. Gastrointestinal Implants

As described herein, the invention provides therapies (e.g., treatment with a metabolic agent, bariatric procedure, or microbiota modulator) to be used in an individual undergoing treatment with a gastrointestinal implant. For example, the gastrointestinal implant can include a sleeve that limits intestinal nutrient absorption. Such gastrointestinal sleeves are known in the art and include those described in U.S. Pat. Nos. 7,267,694, 7,608,114, 7,695,446, 7,678,068, 8,486,153, 7,476,256, 7,815,589, 7,766,973, and 7,976,488. Alternatively, gastrointestinal implants featuring restrictive elements can be used to increase satiety by limiting flow of ingested material (e.g., chyme) through the gastrointestinal tract. Such implants include those described in U.S. Pat. Nos. 7,771,382, 8,920,358, and 7,819,836.

The invention may involve gastrointestinal implants anchored by any method. In some instances, the sleeve may be anchored by tissue-penetrating features, such as barbs or blunt elements (e.g., loops, helices, etc.) that integrate within a gastrointestinal lumen, including, but not limited to, those described in U.S. Pat. Nos. 9,265,596 and 8,834,553. Other tissue-penetrating features that may be useful for, e.g., anchoring a gastrointestinal device in an individual's gastrointestinal tract include, e.g., sutures, staples, or the like. Alternatively, gastrointestinal implants may not include a tissue penetrating feature and may instead be atraumatically positioned within a gastrointestinal tract. Such atraumatic gastrointestinal implants include, but are not limited to, those described in U.S. Pat. Nos. 5,830,584, 7,122,058, 9,278,019, 8,211,186, 8,475,401, 8,109,895, 8,568,488, 7,931,693, 9,060,835, 8,636,683, 8,821,429, 8,048,169, and U.S. Publication Numbers US2014/0296770A1, US2015/0190259A1, US2011/0190905A1, and US2012/0095384A1.

Gastrointestinal implants of the invention can be positioned anywhere in the gastrointestinal tract. In some cases, the implant is anchored distal to the pylorus (e.g., in the duodenum, e.g., at the duodenal bulb, or at or distal to the ampulla of Vader). In other cases, the gastrointestinal implant is anchored at the pylorus (e.g., supported by elements on both proximal and distal sides of the pyloric sphincter). Alternatively, the implant may be substantially positioned within the stomach (e.g., within the antrum or body of the stomach, e.g., to occupy space in the stomach).

III. Combination Therapies with Metabolic Agents

Provided herein are methods of treating a metabolic disorders (e.g., type 2 diabetes, obesity, and related comorbidities (e.g., NASH or NAFLD)), wherein an individual undergoing treatment with a gastrointestinal implant is also treated with a metabolic agent. The metabolic agent in the method of the inventions can be any suitable metabolic agent known in the art or described herein. In some instances, the metabolic agent is an incretin modulator. Incretin modulators that can be used include, for example, glucagon-like peptide-1 (GLP-1) receptor agonists or dipeptidyl peptidase-4 (DPP-4) inhibitors. GLP-1 receptor agonists that can be used include, but are not limited to, liraglutide (NN2211, sold under the brand names VICTOZA® and SAXENDA®), exenatide (sold under the brand names BYETTA®, BYDUREON®, and AMYLIN®), lixisenatide (sold under the brand names LYXUMIA® and ADLYXIN®), dulaglutide (sold under the brand name TRULICITY®), or albiglutide (sold under the brand names EPERZAN® and TANZEUM®), and pharmaceutically acceptable salts thereof. DPP-4 inhibitors that can be used include, but are not limited to, sitagliptin (MK-0431, sold under the brand name JANUVIA®, JANUMET®, JANUMET XR®, and JUVISYNC®), saxagliptin (sold under the brand name ONGLYZA® and KOMBIGLYZE XR®), alogliptin (sold under the brand names NESINA®, VIPIDIA®, KAZANO®, OSENI®, VIPIDOMET® (alogliptin in combination with metformin), and INCRESYNC® (alogliptin in combination with pioglitazone), linagliptin (sold under the brand names TRADJENTA®, GLYXAMBI®, JENTADUETO®, and JENTADUETO XR®), and pharmaceutically acceptable salts thereof.

The metabolic agent of the invention may be administered in any pharmaceutically acceptable formulation containing the metabolic agent and any pharmaceutically acceptable diluents, carriers, or excipients that are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. The compositions may be formulated according to conventional pharmaceutical practice. The concentration of the compound in the formulation will vary depending upon a number of factors, including the dosage of the drug to be administered, and the route of administration.

Administration and Formulations

The methods described herein can be used in any therapeutic or prophylactic context in which the metabolic agent may be useful to the individual undergoing treatment with a gastrointestinal implant. In some instances, the metabolic agent (e.g., GLP-1 receptor agonist or DPP-4 inhibitor) can be administered before, concurrently with, and/or after treatment with the gastrointestinal implant (e.g., before, during or after implantation). For example, the metabolic agent (e.g., GLP-1 receptor agonist or DPP-4 inhibitor) can be administered first followed by implantation of the gastrointestinal device. Alternatively, the gastrointestinal device can be implanted first, followed by administration of the metabolic agent.

In accordance with the methods disclosed herein, the metabolic agent (e.g., GLP-1 receptor agonist or DPP-4 inhibitor) may be provided in any pharmaceutically acceptable formulation and administered in any manner known in the art which renders the metabolic agent biologically available to the subject or sample in effective amounts. The metabolic agent or a pharmaceutical composition including the metabolic agent may be formulated for, e.g., oral administration, intravenous administration, intramuscular administration, intradermal administration, intraarterial administration, topical administration, intravaginal administration, subcutaneous administration, or by inhalation.

In some instances, the metabolic agent (e.g., GLP-1 receptor agonist or DPP-4 inhibitor) of the present invention may be formulated in the form of liquid solutions or suspensions and administered by any parenteral route. Parenteral administration may include but is not limited to intravenous, intra-arterial, intradermal, subcutaneous, intramuscular, intracranial, intraorbital, ophthalmic, intraventricular, intracapsular, intraspinal, intracisternal, or intraperitoneal routes of administration. Pharmaceutical compositions for injection can be formulated using a sterile solution or any pharmaceutically acceptable liquid as a vehicle. Pharmaceutically acceptable vehicles include, but are not limited to, sterile water, physiological saline, or cell culture media (e.g., Dulbecco's Modified Eagle Medium (DMEM), α-Modified Eagles Medium (α-MEM), F-12 medium). For injectable formulations, various effective pharmaceutical carriers are known in the art (See, e.g., Remington: The Science and Practice of Pharmacy, 22nd ed., (2012) and ASHP Handbook on Injectable Drugs, 18th ed., 2014).

In some instances, the metabolic agent (e.g., GLP-1 receptor agonist or DPP-4 inhibitor) of the present invention may be formulated for administration by any enteral route (e.g., orally). In some instances, the metabolic agent (e.g., GLP-1 receptor agonist or DPP-4 inhibitor) can be prepared in the form of an oral formulation. Formulations for oral use can include tablets, caplets, capsules, syrups, or oral liquid dosage forms containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like. Formulations for oral use may also be provided in unit dosage form as chewable tablets, non-chewable tablets, caplets, capsules (e.g., as hard gelatin capsules wherein the active ingredient is mixed with an inert solid diluent, or as soft gelatin capsules wherein the active ingredient is mixed with water or an oil medium).

Dosage

The dosage of the metabolic agent (e.g., GLP-1 agonist or DPP-4 inhibitor) described herein depends on factors including the route of administration, the disease to be treated, and physical characteristics, e.g., age, weight, general health, of the subject (e.g., a human). The dosage may be adapted by the physician in accordance with conventional factors such as the extent of the disease and different parameters of the subject. Typically, the amount of a metabolic agent (e.g. GLP-1 agonist or DPP-4 inhibitor) contained within one or more doses may be an amount that effectively reduces the risk of or treats a metabolic disorders (e.g., type 2 diabetes, obesity, and related comorbidities (e.g., NASH or NAFLD)) in a subject without inducing significant toxicity.

In some instances, the metabolic agent is liraglutide or pharmaceutically acceptable salts thereof (NN2211, sold under the brand names VICTOZA® and SAXENDA®) administered subcutaneously in doses from about 0.006 mg to about 3 mg (e.g., 0.012±0.006 mg, 0.024±0.012 mg, 0.050±0.0.025 mg, 0.075±0.025 mg, 0.1±0.05 mg, 0.15±0.05 mg, 0.2±0.1 mg, 0.4±0.2 mg, 0.6±0.4 mg, 1±0.5 mg, 1.5±0.5 mg, 2±0.5 mg, or 2.5±0.5 mg). In some instances, the metabolic agent is exenatide or pharmaceutically acceptable salts thereof (sold under the brand names BYETTA®, BYDUREON®, and AMYLIN®) administered subcutaneously in doses from about 0.05 µg to about 3 µg (e.g., 0.05±0.01, 0.06±0.02 µg, 0.08±0.04 µg, 0.10±0.05 µg, 0.15±0.05 µg, 0.2±0.1 µg, 0.4±0.2 µg, 0.6±0.2 µg, 0.8±0.2 µg, 1±0.5 µg, 1.5±0.5 µg, 2±1 µg, 3±1 µg, 4±2 µg, 6±2 µg, or 8±2 µg). In some instances, the metabolic agent is lixisenatide or pharmaceutically acceptable salts thereof (sold under the brand names LYXUMIA® and ADLYXIN®) administered subcutaneously in doses from about 0.1 µg to about 20 µg (e.g., 0.15±0.05 µg, 0.2±0.1 µg, 0.4±0.2 µg, 0.6±0.2 µg, 0.8±0.2 µg, 1±0.5 µg, 1.5±0.5 µg, 2±1 µg, 3±1 µg, 4±2 µg, 6±2 µg, 8±2 µg, 10±2 µg, 12±2 µg, 14±2 µg, 16±2 µg, or 18±2 µg). In some instances, the metabolic agent is dulaglutide or pharmaceutically acceptable salts thereof (sold under the brand name TRULIC-ITY®) administered subcutaneously in doses from about 0.008 mg to about 1.5 mg (e.g., 0.016±0.008 mg, 0.024±0.008 mg, 0.050±0.0.025 mg, 0.075±0.025 mg, 0.1±0.05 mg, 0.15±0.05 mg, 0.2±0.1 mg, 0.4±0.2 mg, 0.6±0.4 mg, 1±0.5 mg, 1.5±0.5 mg, 2±0.5 mg, or 2.5±0.5 mg). In some instances, the metabolic agent is albiglutide or pharmaceutically acceptable salts thereof (sold under the brand names EPERZAN® and TANZEUM®) administered subcutaneously in doses from about 0.3 mg to about 50 mg (e.g., 0.5±0.2 mg, 0.7±0.2 mg, 0.9±0.2 mg, 1±0.5 mg, 1.5±0.5 mg, 2±0.5 mg, 2.5±0.5 mg, 3±2 mg, 4±2 mg, 6±2 mg, 8±2 mg, 10±2 mg, 12±2 mg, 14±2 mg, 16±2 mg, 18±2 mg, 20±5 mg, 25±5 mg, 30±5 mg, 35±5 mg, 40±5 mg, or 45±5 mg).

In some instances, the metabolic agent is sitagliptin or pharmaceutically acceptable salts thereof (MK-0431, sold under the brand name JANUVIA®, JANUMET®, JANUMET XR 200 , and JUVISYNC®) orally administered in doses from about 0.25 mg to about 100 mg (e.g., 0.5±0.25 mg, 0.75±0.25 mg, 1±0.5 mg, 1.5±0.5 mg, 2±0.5 mg, 2.5±0.5 mg, 3±2 mg, 4±2 mg, 6±2 mg, 8±2 mg, 10±2 mg, 12±2 mg, 14±2 mg, 16±2 mg, 18±2 mg, 20±5 mg, 25±5 mg, 30±5 mg, 35±5 mg, 40±5 mg, 45±5 mg, 50±10 mg, 60±10 mg, 70±10 mg, 80±10 mg, or 90±10 mg). In some instances, the metabolic agent is saxagliptin or pharmaceutically acceptable salts thereof (sold under the brand name ONGLYZA®, KOMBIGLZE XR®) orally administered in doses of about 0.025 mg to about 5 mg (e.g., 0.5±0.25 mg, 0.75±0.25 mg, 1±0.25 mg, 1.5±0.5 mg, 2±0.5 mg, 2.5±0.5 mg, 3±0.5 mg, 3.5±0.5 mg, 4±0.5 mg, or 4.5±0.5 mg). In some instances, the metabolic agent is alogliptin or pharmaceutically acceptable salts thereof (sold under the brand names NESINA®, VIPIDIA®, KAZANO®, OSENI®, VIPIDOMET® (alogliptin in combination with metformin), and INCRESYNC® (alogliptin in combination with pioglitazone)) orally administered in doses of about 0.06 mg to about 25 mg (e.g., 0.05±0.01 mg, 0.06±0.02 mg, 0.08±0.04 mg, 0.10±0.05 mg, 0.15±0.05 mg, 0.2±0.05 mg, 0.25±0.05 mg, 0.5±0.05 mg, 0.35±0.05 mg, 0.4±0.2 mg, 0.6±0.2 mg, 0.8±0.2 mg, 1±0.5 mg, 1.5±0.5 mg, 2±1 mg, 3±1 mg, 4±2 mg, 6±2 mg, 8±2 mg, 10±2 mg, 15±5 mg, or 20±5 mg). In some instances, the metabolic agent is linagliptin or pharmaceutically acceptable salts thereof (sold under the brand names TRADJENTA®, GLYXAMBI®, JENTADUETO®, and JENTADUETO XR®) orally administered in doses of about 0.025 mg to about 5 mg (e.g., 0.5±0.25 mg, 0.75±0.25 mg, 0.5±0.0.2 mg, 0.6±0.2 mg, 0.8±0.2 mg, 1±0.5 mg, 1.5±0.5 mg, 2±0.5 mg, 2.5±0.5 mg, 3±0.5 mg, 3.5±0.5 mg, 4±0.5 mg, or 4.5±0.5 mg).

Any pharmaceutically acceptable formulation of the metabolic agent of the present invention can be administered one or more times per day (e.g., 1, 2, 3, or 4 times per day), one or more times per week (e.g., 1, 2, 3, 4, 5, or 6 days a week), or one or more times per month (e.g., 1, 2, or 3 weeks per month). The formulations can be administered to a subject in therapeutically effective amounts. The preferred dosage of drug to be administered is likely to depend on variables such as the type and extent of the disorder, the overall health status of the particular subject, the specific compound being administered, the excipients used to formulate the compound, and its route of administration. Single or multiple administrations of the metabolic agent of the invention including an effective amount can be carried out with dose levels and patterns being selected by the treating physician. The dose and administration schedule can be determined and adjusted based on the severity of the disease or condition in the subject, which may be monitored throughout the course of treatment according to the methods commonly practiced by clinicians or those described herein. The compounds of the present invention may be used in combination with other conventional methods of treatment (e.g., in combination with metformin) or therapy or may be used separately from conventional methods of treatment or therapy.

IV. Combination Therapies with Bariatric Procedures

Bariatric Procedures

Provided herein are methods of treating metabolic disorders (e.g., type 2 diabetes, obesity, and related comorbidities (e.g., NASH or NAFLD)), wherein an individual undergoing treatment with a gastrointestinal implant is treated with one or more bariatric procedures. Bariatric procedures refer to procedures that modify the function, size, and/or shape of the gastrointestinal tract including, but not limited to, gastric banding, sleeve gastrectomy, GI bypass procedures (e.g., roux-en-Y, biliary duodenal bypass, loop gastric bypass), intragastric balloon, vertical banded, gastroplasty, and biliopancreatic diversion.

In some instances, the bariatric procedure is a restrictive bariatric procedure. For example, the restrictive bariatric procedure can restrict space in the gastrointestinal tract indirectly (e.g., by providing a space-occupying device) or directly (e.g., by modifying the shape and/or size of the stomach). In some instances, the restrictive bariatric procedure can provide an intragastric balloon as a space-occupying device. Alternatively, the restrictive bariatric procedure can be a gastroplasty procedure that modifies the size or shape of the stomach. For example, the gastroplasty procedure can involve the placement of transmural tissue anchor plications in the gastric fundus and body (e.g., USGI® Primary Obesity Surgery Endolumenal (POSE) or other procedures using the USGI® Incisionless Operating Platform). In some instances, the bariatric procedure can be performed on the same day that the gastrointestinal sleeve is implanted in the subject (e.g., within 15 min, 30 min, 1 hr, 2 hr, 4 hr, 6 hr, or 12 hr, 24 hr before or after implantation).

Alternatively, the bariatric procedure can be performed on a different day before or after the implantation of the gastrointestinal sleeve (e.g., within 36 hr, 2 days, 3 days, 4, days, 5 days, 1 weeks, 2, weeks, 3 weeks, 1 month, 2 months, 3 months, 4 months, 5 months, or 6 months before or after implantation).

V. Combination Therapies with Microbiota Modulators

Provided herein are methods of treating metabolic disorders (e.g., type 2 diabetes, obesity, and related comorbidities (e.g., NASH or NAFLD)), wherein an individual undergoing treatment with a gastrointestinal implant is also treated with an agent that modulates the microbiota of the individual (e.g., an agent that increases the presence or activity of beneficial bacteria and/or suppresses the presence or activity of pathogenic bacteria). As described herein, the microbiota modulator can include microbial agents (e.g., bacterial or fungal cells, bacteriophage, probiotics), non-microbial agents (e.g., compounds, pharmaceutical substances, prebiotics), or a combination thereof. For example, the treatment can include administration of (i) one or more micro-organisms, (ii) one or more compounds or agents, such as prebiotics that foster the growth, survival, persistence, transit or existence of microbiota, or a combination thereof. The microbiota modulator composition may alternatively or additionally comprise a selective microbial growth inhibitor. The microbiota modulator may alter, for example, the diversity, composition, or abundance (e.g., increase or decrease the relative level) of microbiota in the gastrointestinal tract of the subject, wherein the level of beneficial bacteria is increased and/or the level of harmful bacteria is reduced. In particular, the microbiota modulator may alter the gastrointestinal microbiota in in such a manner that leads to synergistic health benefit for the individual, such as greater weight loss or improved blood glucose levels, than when the individual is treated with the gastrointestinal implant alone or the microbiota modulator alone.

The microbiota modulator can be administered at any time that benefits the subject during treatment with the gastrointestinal implant (e.g., before, during, or after implantation). The microbiota modulator can alter microbiota in the subject to achieve a diversity, composition, or abundance of microbiota that is beneficial to the individual in the context of treating metabolic disorders (e.g., type 2 diabetes, obesity, and related comorbidities (e.g., NASH or NAFLD)). In one particular example, the microbiota modulator can alter the microbiota of the recipient to make it similar (e.g., 1%, 2%, 5%, 10%, 20%, 30%, 40%, 50%, 60%, 70%, 80%, or 100% similar) that of a healthy individual (e.g., an individual without metabolic disorders (e.g., type 2 diabetes, obesity, and related comorbidities (e.g., NASH or NAFLD)). Alternatively, the microbiota modulator can alter the microbiota of the recipient to make it similar (e.g., 1%, 2%, 5%, 10%, 20%, 30%, 40%, 50%, 60%, 70%, 80%, or 100% similar) to that of a subject who is responsive to a bariatric procedure).

Microbial Agents (e.g., Probiotics)

The microbiota modulator composition may include one or more microbial strains. Such microbial strains could be bacterial and fall within the scope of what is typically considered in the art to be a probiotic. The microbiota modulator composition may alternatively or additionally comprise a growth medium for one or more microbial strains (e.g., strains already present in the individual or included as part of microbiota modulator composition). Microbial agents can include whole bacterial or fungal cells (e.g., viable (live) cells, dormant cells (e.g., endospores), inactivated cells, dead cells, or any combination thereof) or substances that support (e.g., promote growth, diversity, or maintenance of) a beneficial level or composition of microbiota in the gastrointestinal tract of a subject undergoing treat with a gastrointestinal implant. The microbial cells may be derived from microbial populations (e.g., one or more phyla, genera, species, or strains) found in nature (e.g., in a mammalian gastrointestinal tract) or derived from strains of bacteria not typically found in nature (e.g., laboratory strains). The bacterial cells can contain a single phylum, genus, or species of bacteria or, alternatively, multiple phyla, genera, or species of bacteria. The bacteria that can be used in the treatment methods (e.g., bacteria common to the gut, colon or intestine) include, but are not limited to, bacterial phyla such as Bacteroidetes, Proteobacteria, Firmicutes, Tenericutes and Verrucomicrobia; bacterial classes such as Mollicutes; bacterial orders such as Bacteroidales, Enterobacteriales, Erysipelotrichales, Clostridialel and Verrucomicrobiales; bacterial genera such as *Alistipes, Escherichia, Clostridium, Allobaculum*, and *Akkermansia*; or a combination thereof.

A microbial agent (e.g., bacterial or fungal cells) can be administered in a probiotic formulation that includes, for example, food-grade microorganisms (e.g., viable, semi-viable or weakened, and/or non-replicating fungi or bacteria), metabolites, microbial cell preparations or components of microbial cells that could confer health benefits on the host subject when administered in adequate amounts, more specifically, that beneficially affect a host by improving its intestinal microbial balance, leading to effects on the health or well-being of the host (e.g., treatment of metabolic disorders (e.g., type 2 diabetes, obesity, and related comorbidities (e.g., NASH or NAFLD))). The probiotic organism can be formulated in any therapeutically effective formulation, e.g., for treating metabolic disorders (e.g., type 2 diabetes, obesity, and related comorbidities (e.g., NASH or NAFLD)) and administered by any therapeutically effective route (e.g., oral or rectal), including any of those described above (See section III of detailed description). For example, the probiotic can be administered as part of a supplement or pharmaceutical composition. For example, the probiotic can be formulated as a culture in water or another liquid or semisolid medium in which the probiotic remains viable; or as a freeze-dried powder containing the probiotic organism. Alternatively, the probiotic-containing composition can be a liquid or semi-solid food. For example, the probiotic-containing composition is a dairy or non-dairy food. In yet other embodiments, the probiotic-containing composition is yogurt, butter, cheese, infant formula, or ice cream.

In some instances, food grade bacteria or fungi can be selected from the group consisting of *Bifidobacterium, Lactobacillus, Lactococcus, Enterococcus, Streptococcus Ascomycota, Deuteromycota, Debaryomyces, Kluyveromyces, Saccharomyces, Yarrowia, Zygosaccharomyces, Candida,* and *Rhodotorula*; preferentially lactic acid bacteria and bifidobacteria, or mixtures thereof; and/or in particular may be selected from the group consisting of *Bifidobacterium longum, Bifidobacterium lactis, Bifidobacterium animalis, Bifidobacterium breve, Bifidobacterium infantis, Lactobacillus acidophilus, Lactobacillus casei, Lactobacillus salivarius, Lactococcus lactis, Lactobacillus reuteri, Lactobacillus rhamnosus, Lactobacillus paracasei, Lactobacillus johnsonii, Lactobacillus plantarum, Lactobacillus sali-*

*varius, Enterococcus faecium, Saccharomyces cerevisia, Saccharomyces boulardii* and *Lactobacillus reuteri* or mixtures thereof, preferably selected from the group consisting of *Lactobacillus johnsonii, Bifidobacterium longum, Bifidobacterium longum, Bifidobacterium lactis, Lactobacillus paracasei, Lactobacillus rhamnosus* GG, *Lactobacillus rhamnosus*, and mixtures thereof. Non-limiting examples of probiotics include *Aerococcus, Aspergillus, Bacillus, Bacteroides, Clostridium, Fusobacterium, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Staphylococcus, Streptococcus, Torulopsis, Weissella*, or a combination thereof.

Fecal Microbiota Transplant

The microbiota modulator described herein can comprise whole bacterial cells supplied via a fecal sample or isolate thereof (e.g., a fecal sample containing an active bacterial population and/or substances to support said population). The fecal sample or isolate thereof can be provided in the form of a fecal microbiota transplant, wherein the fecal matter is taken from a donor and given to a recipient undergoing treatment with the gastrointestinal implant. The donor can be a healthy individual (e.g., a person who does not have metabolic disorders (e.g., type 2 diabetes, obesity, and related comorbidities (e.g., NASH or NAFLD))). Alternatively, the fecal transplant donor can be any individual with a composition of gastrointestinal microbiota that may be beneficial for the recipient (e.g., a subject undergoing treatment with a gastrointestinal implant). For example, the donor can be a subject who is or was previously responsive to a bariatric procedure. The microbiota modulator can alter microbiota in the recipient to mimic or make it similar to microbiota found in the donor, such as a subject that is responsive to a surgical procedure like gastric bypass or other gastrointestinal bariatric or metabolic procedures. In some instances, the existing microbiota of the recipient does not need to be cleared prior to administration of microbiota modulator. Alternatively, clearance of the existing microbiota of the recipient microbiota may be necessary. Methods for clearance of existing microbiota are known in the art. In one example, clearance can be accomplished by administering a cocktail of antibiotics for one week until a day prior to the fecal microbiota transplant (e.g., metronidazole (1000 mg twice daily), rifaximin (550 mg twice daily), vancomycin (500 mg twice daily), and neomycin (1000 mg twice daily)).

Non-Microbial Agents (e.g., Prebiotics)

The microbiota modulator described herein can include one or more prebiotics. The prebiotic can be a substance (e.g., a synthetic or natural substance in a food, a supplement, or a pharmaceutical composition) that selectively promotes the growth of beneficial bacteria or inhibits the growth or mucosal adhesion of pathogenic bacteria in the gastrointestinal tract. Prebiotics may be fermented or metabolized by the gastrointestinal microflora and/or by probiotics. Further, the administration of one or more prebiotic compounds may selectively enhance the relative abundance or growth of one or more targeted microbiota.

The prebiotic in the methods of the invention can include, but is not limited to, polyphenols, saccharides, mucopolysaccharides, oligosaccharides, polysaccharides, amino acids, peptides, polypeptides, lipids, vitamins, or nutrient precursors. Additional non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof. Other examples of prebiotics can include bacterial cell wall components such as peptidoglycans, bacterial nucleic acids such as DNA and RNA, bacterial membrane components, and bacterial structural components such as proteins, carbohydrates, lipids and combinations of these such as lipoproteins, glycolipids and glycoproteins. Additional examples can also include organic acids, inorganic acids, bases, proteins and peptides, enzymes and co-enzymes, amino acids and nucleic acids, carbohydrates, lipids, glycoproteins, lipoproteins, glycolipids, vitamins, bioactive compounds, metabolites containing an inorganic component, small molecules, for example nitrous molecules or molecules containing a sulphurous acid, resistant starch, potato starch or high amylose starch, modified starches (including carboxylated starches, acetylated, propionated, and butyrated starches), non-digestible oligosaccharides such as fructooligosaccharides. Prebiotics also include dietary fibers.

Administration

The microbiota modulator described herein may be formulated and administered by any therapeutically effective or pharmaceutically acceptable methods known in the art (e.g., see section III of detailed description). Specifically, the microbiota modulator may be administered by any method suitable for depositing in the gastrointestinal tract a subject (e.g., in an oral supplement or in food). Examples of routes of administration include, but are not limited to, rectal administration (e.g., by suppository, enema, upper endoscopy, upper push enteroscopy, or colonoscopy), intubation through the nose or the mouth (e.g., by nasogastric tube, nasoenteric tube, or nasal jejunal tube), or oral administration (e.g., by a solid such as a pill, tablet, or capsule, or by liquid). Oral compositions may include an inert diluent or an edible carrier. For the purpose of oral therapeutic administration, the composition can be incorporated with any pharmaceutically acceptable excipients and used in the form of tablets, or capsules, e.g., gelatin capsules. Oral compositions can also be prepared by combining a composition with a food. In one embodiment a food used for administration is chilled, for instance, ice cream or milk. Other ingredients may be added to a formulation to provide desired characteristics such as flow, compression, hardness, and taste.

EXAMPLES

Example 1. Use of a Metabolic Agent in a Subject Undergoing Treatment with a Gastrointestinal Implant An individual with type 2 diabetes is undergoing treatment with a gastrointestinal implant. The individual has a body mass index (BMI)>30 mg/m$^2$ at the initiation of treatment. The individual fails to achieve a reduction in weight, HbA1c, blood and/or urine glucose during the first 3 months of treatment. In the presence of gastrointestinal implant, individual is administered the GLP-1 agonist, liraglutide. Liraglutide is given at an effective dose of 1.2 mg daily. After 9 months of combination therapy consisting of gastrointestinal implant plus liraglutide, individual attains >2.0% reduction in HbA1c, >10 kg loss of weight, >10.0% reduction in total body weight, and improvements in glucose control. The combination of gastrointestinal implant and liraglutide is found to be superior to gastrointestinal implant or liraglutide alone.

Example 2. Restrictive Bariatric Surgery in a Subject Undergoing Treatment with a Gastrointestinal Implant An individual with type 2 diabetes has a body mass index (BMI)>35 mg/m$^2$. The individual is recommended for therapy with a gastrointestinal implant and space-occupying device (e.g., a device that displace volumes and induces gastric distention, but may also alter gastrointestinal motility, nutrient transit, and hormone levels). The gastrointestinal implant is delivered according to methods known in the art. The space-occupying device is delivered into the patients stomach either concurrently with or separately from the gastrointestinal implant. Once a patient has improved in blood glucose levels and lost the desired amount of weight, or if efficacy plateaus, or if patient safety is compromised, the inflated expandable member is deflated and removed by disconnecting a tether (for concurrent delivery) prior to removal. Gastrointestinal implant can be removed or remain in place for further treatment. The combination of gastrointestinal implant and space-occupying device is found to be superior to gastrointestinal implant or space-occupying device alone.

Example 3. Gastroplasty Surgery in a Subject Undergoing Treatment with a Gastrointestinal Implant A restrictive procedure is performed on an individual to remodel the stomach via suturing, stapling, or tissue anchor placement to reduce gastric volume or bypass an absorptive surface of the small intestine. The individual is recommended for therapy with a gastrointestinal implant. The gastrointestinal implant is delivered according to conventional methods known in the art or concurrent with the restrictive procedure (i.e. tissue anchor placement with endoscope). The combination of gastrointestinal implant and restrictive procedure facilitates durable weight loss and comorbidity improvement compared to gastrointestinal implant or restrictive procedure alone.

Example 4. Fecal Microbiota Transplant in a Subject Undergoing Treatment with a Gastrointestinal Implant An individual with type 2 diabetes is undergoing treatment with a gastrointestinal implant. A fecal transplant is recommended to supplement normalization of blood glucose levels and weight loss. A portion of the patient's microbiome is sequenced and may be used to detect the presence or absence of specific candidate bacteria that are biomarkers for a metabolic disorder (e.g., type 2 diabetes and/or obesity). An effective dose of a bacterial composition from a lean donor is administered by rectal or enteric means for an effective time period or for the duration of treatment with the gastrointestinal implant. The bacterial composition may be administered with other agents, including anti-microbial agents and prebiotics. The patient is recommended a diet regimen to support colonization of fecal microbes from lean donor. The gastrointestinal implant is removed after 1 year of treatment. At the conclusion of therapy, combination of gastrointestinal implant and fecal transplant is found to facilitate durable weight loss and comorbidity improvement than gastrointestinal implant or fecal transplant alone.

Other Embodiments

All publications, patents, and patent applications mentioned in this specification are herein incorporated by reference to the same extent as if each independent publication or patent application was specifically and individually indicated to be incorporated by reference. In the event of conflicting definitions between this and any reference incorporated herein, the definition provided herein applies.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims.

Other embodiments are within the claims.

What is claimed is:

1. A method of treating a metabolic disorder in an individual undergoing treatment with a gastrointestinal implant configured to bypass at least part of a small intestine the method comprising administering one or more metabolic agents to the individual in an effective amount and for a duration to treat the metabolic disorder, wherein the gastrointestinal implant comprises a wave anchor and a sleeve with a length from about 1 ft to about 5 ft.

2. The method of claim 1, wherein the one or more metabolic agents comprises an incretin modulator, wherein the incretin modulator is a glucagon-like peptide-1 (GLP-1) receptor agonist or a dipeptidyl peptidase-4 (DPP-4) inhibitor.

3. The method of claim 2, wherein:
   (a) the GLP-1 receptor agonist is liraglutide, exenatide, lixisenatide, dulaglutide, or albiglutide; and/or
   (b) the DPP-4 inhibitor is sitagliptin, saxagliptin, alogliptin, or linagliptin.

4. The method of claim 3, wherein:
   (a) the liraglutide is administered at a dose from 0.006 mg to 3 mg;
   (b) the exenatide is administered at a dose from 0.05 µg to 10 µg;
   (c) the lixisenatide is administered at a dose from 0.1 µg to 20 µg;
   (d) the dulaglutide is administered at a dose from 0.0075 mg to 1.5 mg; and/or
   (e) the albiglutide is administered at a dose from 0.3 mg to 50 mg.

5. The method of claim 3, wherein:
   (a) the sitagliptin is administered at a dose from 0.25 mg to 100 mg;
   (b) the saxagliptin is administered at a dose from 0.025 mg to 5 mg;
   (c) the alogliptin is administered at a dose of 0.0625 mg to 25 mg; and/or
   (d) the linagliptin is administered at a dose of 0.025 ma to 5 mg.

6. The method of claim 1, wherein the one or more metabolic agents is administered by an enteral route or by a parenteral route.

7. The method of claim 1, wherein the one or more metabolic agents;
   (a) is administered one or more times per month;
   (b) is administered one or more times per week; or
   (c) is administered one or more times per day.

8. The method of claim 1, wherein the one or more metabolic agents is administered prior to treatment with the gastrointestinal implant or during treatment with the gastrointestinal implant.

9. A method of treating a metabolic disorder in an individual undergoing treatment with a gastrointestinal implant configured to bypass at least part of a small intestine, the method comprising one or more bariatric procedures to treat the metabolic disorder.

10. The method of claim 9, wherein the one or more bariatric procedures comprises a restrictive bariatric procedure comprising:
    (a) providing a space-occupying device to an individual, wherein the space-occupying device is an intragastric balloon; or
    (b) a gastroplasty procedure, wherein the gastroplasty procedure comprises placing transmural tissue anchor plications in the gastric fundus and body.

11. A method of treating a metabolic disorder in an individual undergoing treatment with a gastrointestinal implant configured to bypass at least part of a small intestine, the method comprising administering one or more microbiota modulators to an individual in an effective amount and for a duration to treat the metabolic disorder, wherein the gastrointestinal implant comprises a sleeve with a length from about 1 ft to about 5 ft.

12. The method of claim 11, wherein the one or more gastrointestinal microbiota modulators comprises:
    (a) treatment with one or more species of bacteria; or
    (b) treatment with one or more bacteriophage.

13. The method of claim 12, wherein the treatment with one or more species of bacteria is provided by a fecal microbiota transplant.

14. The method of claim 11, wherein the one or more gastrointestinal microbiota modulators comprises:
    (a) a prescribed diet regimen, wherein the prescribed diet regimen comprises a food enriched in one or more polyphenols, saccharides, polysaccharides, peptides, polypeptides, lipids, or any combination thereof or a food enriched in one or more species of bacteria; or
    (b) a dietary supplement, wherein the dietary supplement is a prebiotic supplement or a probiotic supplement, wherein the prebiotic supplement comprises a polyphenol, saccharide, polysaccharide, peptide, polypeptide, lipid, or any combination thereof.

15. The method of claim 11, wherein the one or more gastrointestinal microbiota modulators is administered prior to treatment the gastrointestinal implant or during treatment with the gastrointestinal implant, wherein the one or more gastrointestinal microbiota modulators is an agent that increases survival of beneficial gastrointestinal microbiota of the individual or modifies a composition of pathogenic gastrointestinal microbiota of the individual.

16. The method of claim 11, wherein the one or more gastrointestinal microbiota modulators is administered by an enteral route or by a parenteral route.

17. The method of claim 11, the method comprising (a) providing a gastrointestinal implant to the individual, wherein the gastrointestinal implant comprises a sleeve, wherein the gastrointestinal implant is configured to bypass at least part of the small intestine, wherein at least part of the gastrointestinal implant is configured for implantation within a gastrointestinal tract at or distal to a pylorus of the individual and (b) recommending:
    (i) one or more bariatric procedures to treat a metabolic disorder,
    (ii) administration of one or more metabolic agents in an effective amount and for a duration to treat the metabolic disorder, or
    (iii) administration of one or more microbiota modulators in an effective amount and for a duration to treat the metabolic disorder.

18. The method of claim 11, wherein the metabolic disorder is type 2 diabetes, obesity, non-alcoholic steatohepatitis (NASH), or non-alcoholic fatty liver disease (NAFLD).

19. The method of claim 17, wherein the gastrointestinal sleeve comprises a wave anchor.

20. The method of claim 19, wherein the wave anchor is configured to reside distal to a pylorus of the individual.

* * * * *